United States Patent
Galusha et al.

(10) Patent No.: US 8,423,388 B1
(45) Date of Patent: Apr. 16, 2013

(54) GUI FOR RISK PROFILES

(75) Inventors: Larry J. Galusha, Southfield, MI (US);
Kathleen Burns, Palos Heights, IL (US);
Carol A. Ungaretti, Oak Park, IL (US)

(73) Assignee: AON Global Risk Research Limited, Hamilton (BM)

( * ) Notice: Subject to any disclaimer, the term of this patent is extended or adjusted under 35 U.S.C. 154(b) by 0 days.

(21) Appl. No.: 13/351,989

(22) Filed: Jan. 17, 2012

(51) Int. Cl.
*G06Q 40/00* (2006.01)
(52) U.S. Cl.
USPC .................................. 705/4; 705/30
(58) Field of Classification Search .................. 705/3–44
See application file for complete search history.

(56) References Cited

U.S. PATENT DOCUMENTS

| | | | |
|---|---|---|---|
| 5,956,691 A * | 9/1999 | Powers | 705/4 |
| 6,546,979 B2 * | 4/2003 | Jonkka | 144/341 |
| 7,249,077 B2 * | 7/2007 | Williams et al. | 705/35 |
| 7,698,158 B1 * | 4/2010 | Flagg | 705/4 |
| 8,112,288 B1 * | 2/2012 | Paul et al. | 705/2 |
| 8,170,944 B1 * | 5/2012 | Kruk et al. | 705/36 R |
| 8,265,963 B1 * | 9/2012 | Hanson et al. | 705/4 |
| 2011/0166883 A1 * | 7/2011 | Palmer et al. | 705/3 |

OTHER PUBLICATIONS

"Early Claim Identification—A Proactive cost mitigation strategy delivering proven results," AON Brochure, Oct. 12, 2011.

* cited by examiner

*Primary Examiner* — Frantzy Poinvil
(74) *Attorney, Agent, or Firm* — Jennifer E. Lacroix, Esq.; DLA Piper US LLP

(57) ABSTRACT

A memory device stores machine-readable instructions executable by a processor to cause the processor to graphically depict on a display device a first category of risk analysis data related to a plurality of insurance claims. The processor also causes the display to graphically depict a relationship between a first analysis result and a first benchmark value corresponding to the first analysis result, and graphically depict one or more user controls for selecting a second category of risk analysis data.

21 Claims, 9 Drawing Sheets

| METRIC | RESULTS | RISK INDICATION | EXPLANATION | RECOMMENDATION |
|---|---|---|---|---|
| | | 208 | | |
| | | 208 | | |
| | | 208 | | |
| | | 208 | | |
| | | 208 | | |
| | | 208 | | |
| | | 208 | | |
| | | 208 | | |

*FIG. 3*

GUI FOR RISK PROFILES

FIELD OF THE DISCLOSURE

The present disclosure relates to assessing cost of risk for a business entity and, in particular, to determining a risk profile related to the total cost of risk for an organization with the goal of identifying and mitigating key loss cost drivers.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Businesses employ a variety of strategies for assessing risks and costs associated with operation, which include, among others, risks and costs related to insurance and, specifically, insurance premiums, retained losses, and administrative expenses. One metric used by organizations to quantify risk is the total cost of risk (TCOR). Methods of calculating TCOR vary by organization, by industry, and by type of risk being assessed. Additionally, the results of TCOR calculations are often difficult to interpret and/or fail to provide useful guidance for identifying key loss cost drivers (i.e., the most significant loss costs) and decreasing the total cost of risk.

SUMMARY

A memory device stores machine-readable instructions executable by a processor. The instructions cause the processor to retrieve a first set of data from a database, the data including information about a number of insurance claims. The instructions also cause the processor to perform an analysis of the first set of data to determine a first result associated with a first key performance indicator. The instructions cause the processor to obtain a first set of benchmark values corresponding to the first key performance indicator, and to compare the first result to the first set of benchmark values to determine the relationship of the first result to the set of benchmark values. The determined relationship is sent to a display device. In various embodiments, the key performance indicator may be one of: a percentage of workers compensation claims that include temporary total disability (TTD) payments; an average number of days per TTD claim; an average value of indemnity claims; a medical-to-indemnity conversion rate; a claim closure rate for workers compensation claims; an average time between a date of loss and a date reported to a third party; a percentage of total claim payments attributable to medical costs; a percentage of medical costs attributable to pharmacy costs; a PPO penetration rate; a percentage of claims litigated; a percentage of total claim payments attributable to expenses; a percentage of total claim payments attributable to legal expenses; a trend relationship related to an actuarially based claim frequency rate; a variance related to an incidence rate of Occupational Safety & Health Administration (OSHA) claims; a variance related to a lost work date rate; and a loss rate calculated based on claim frequency and claim severity.

In some embodiments, the instructions cause the processor to analyze one or more second sets of data to determine one or more second results associated with one or more second key performance indicators and to obtain one or more second sets of benchmark values against which to compare each of the one or more second results. The determined relationships between each of the second results and the second sets of benchmark values are depicted on the display device.

The first key performance indicator may, in some embodiments, be associated with a risk indication according to the comparison of the first result to the first benchmark value, and the risk indication may be displayed on the display device. The second key performance indicators may also be associated with respective risk indications according to the respective comparisons of each against the second benchmark values, and the risk indications displayed on the display device.

In another embodiment, a memory device stores machine-readable instructions executable by a processor. The instructions cause the processor to graphically depict on a display device a first category of risk analysis data related to a plurality of insurance claims, and to graphically depict on the display device a relationship between a first analysis result and a first benchmark value corresponding to the first analysis result. Further, the instructions cause the processor to graphically depict on the display device one or more user controls for selecting a second category of risk analysis data. The first analysis result is one of the group consisting of: a percentage of workers compensation claims that include temporary total disability (TTD) payments; an average number of days per TTD claim; an average value of indemnity claims; a medical-to-indemnity conversion rate; a claim closure rate for workers compensation claims; an average time between a date of loss and a date reported to a third party; a percentage of total claim payments attributable to medical costs; a percentage of medical costs attributable to pharmacy costs; a PPO penetration rate; a percentage of claims litigated; a percentage of total claim payments attributable to expenses; a percentage of total claim payments attributable to legal expenses; a trend relationship related to an actuarially based claim frequency rate; a variance related to an incidence rate of Occupational Safety & Health Administration (OSHA) claims; a variance related to a lost work date rate; and a loss rate. Depicting the relationship between the first analysis result and the first benchmark value may include depicting for each of one or more KPIs associated with the first category at least a value calculated for the KPI and a comparison of the calculated value to a benchmark value.

In some embodiments, the depicted information includes for each KPI depicting one or more historical values corresponding to the calculated value. In some embodiments, the instructions cause the processor to graphically depict for each KPI a relationship between each of the data subsets related to the KPI and/or to receive a user input selecting one or the plurality of data subsets and display the selected data subset in response to the received user input.

BRIEF DESCRIPTION OF THE DRAWINGS

FIG. 3 illustrates a first aspect of an embodiment of a risk profile report in accordance with the present description;

DETAILED DESCRIPTION

Although the following text sets forth a detailed description of numerous different embodiments, it should be understood that the legal scope of the disclosure is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean..." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. 112, sixth paragraph.

Figure 1:
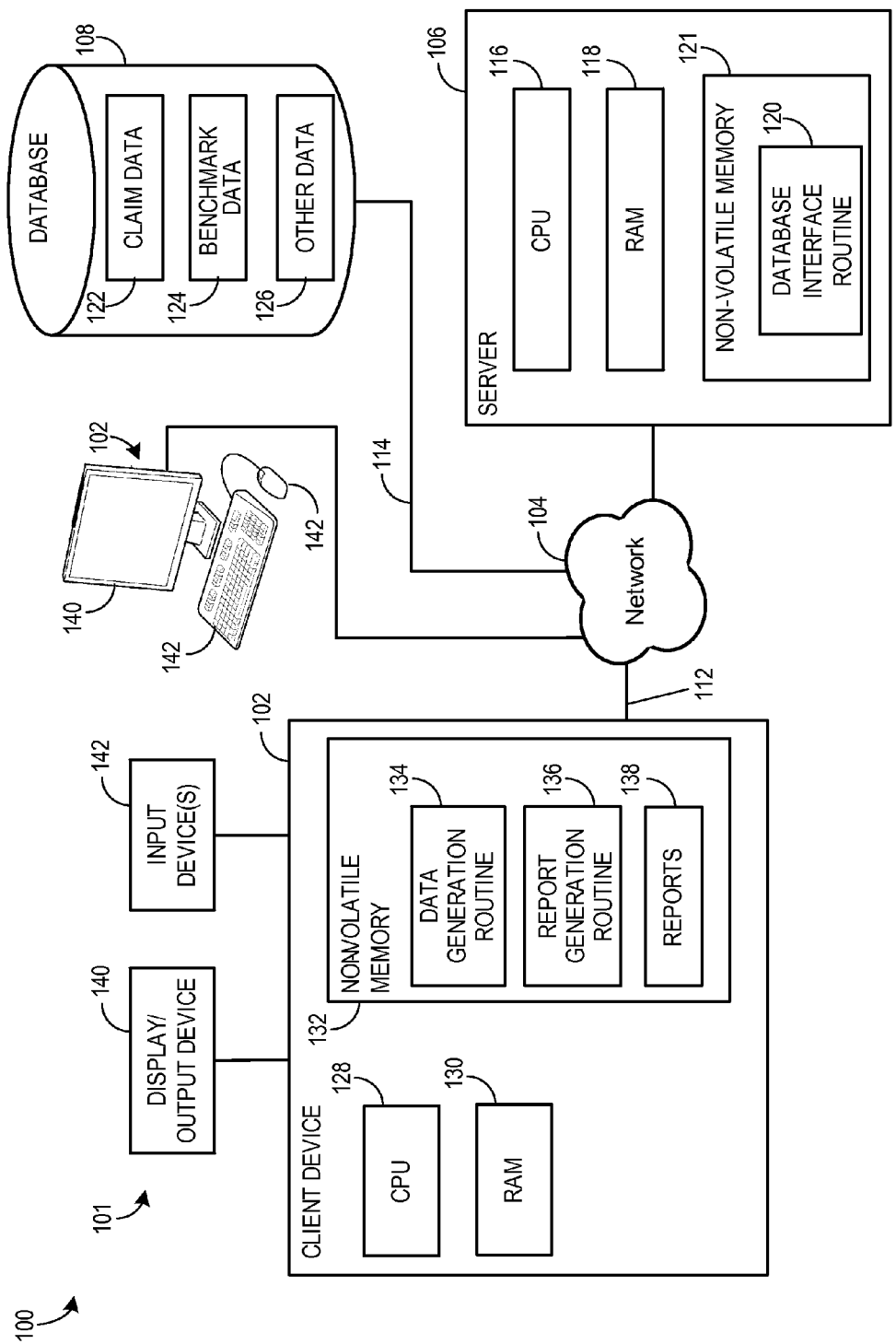
FIG. 1 is a block diagram of an embodiment of a system for generating a risk profile report in accordance with the present description.

FIG. 1 illustrates an exemplary embodiment 101 of a system 100 for assessing risk and generating a risk profile for an organization. Generally, the system 100 may include one or more client devices 102, a network 104, a server 106, and a database 108. Each client device 102 may be communicatively coupled to the network 104 by one or more wired or wireless network connections 112, which may be, for example, a connection complying with a standard such as one of the IEEE 802.11 standards ("Wi-Fi"), the Ethernet standard, or any other appropriate network connection. Similarly, the database 108 and the server 106 are communicatively coupled to the network 104 via one or more connections 114. As will be understood, the network 104 may be a local area network (LAN) or a wide-area network (WAN). That is, network 104 may include only local (e.g., intra-organization) connections or, alternatively, the network 104 may include connections extending beyond the organization and onto one or more public networks (e.g., the Internet). In some embodiments, for example, the client device 102, the server 106, and the database 108 may be within the network operated by a single company (Company A). In other embodiments, for example, the client device(s) 102 may be on a network operated by Company A, while the server 106 and the database 108 may be on a network operated by a second company (Company B), and the networks of Company A and Company B may be coupled by a third network such as, for example, the Internet.

In any event, the server 106 includes a CPU or processor 116, a random-access memory (RAM) 118 and, in an embodiment, a database interface routine 120 for accessing records stored in the database 108. For example, the client device 102 may request records from the database 108 via the server 106. The database interface routine 120 is a routine, executable by the processor 116 and comprising a series of compiled or compilable machine-readable instructions stored in a memory 121 in the server 106. Alternately, the client device 102 may, in some embodiments, directly access records stored in the database 108, without the need of the server 106. The records stored in the database 108 may include claim data 122, benchmark data 124, and other data 126, as described in greater detail below.

Referring still to FIG. 1, the client device 102 includes a processor 128 (CPU), a RAM 130, and a non-volatile memory 132. The non-volatile memory 132 may be any appropriate memory device including, by way of example and not limitation, a magnetic disk (e.g., a hard disk drive), a solid state drive (e.g., a flash memory), etc. Additionally, it will be understood that, at least with regard to FIG. 1, the database 108 need not be separate from the client device 102. Instead, in some embodiments, the database 108 is part of the non-volatile memory 132 and the data 122, 124, 126 may be stored as data within the memory 132. For example, the data 122 may be included as data in a spreadsheet file stored in the memory 132, instead of as data in the database 108. In addition to storing the records of the database 108 (in some embodiments), the memory 132 stores program data and other data necessary to create risk profiles and generate risk profile reports. For example, in an embodiment, the memory 132 stores a spreadsheet application 134 and a report application 136. The spreadsheet application 134 may manipulate, tabulate, and calculate data to generate information of the risk profile, while the report application may compile the information generated by the spreadsheet application 134 and format it for output to the user. Of course, there is no requirement that the application 134 be a spreadsheet application. Instead the application 134 can be any application programmed to access data records from the database 108 and manipulate, tabulate, and calculate the information of the risk profile. In still another embodiment, the application 134 and the application 136 may be part of the same software module (i.e., a single application may retrieve the data, generate the information of the risk profile, and generate the report. Regardless, each of the applications 134, 136 is a routine, executable by the processor 128 and comprising a series of compiled or compilable machine-readable instructions stored in the memory 132. Additionally, the memory 132 may store generated reports 138 in the memory 132. One or more display/output devices 140 (e.g., printer, display, etc.) and one or more input devices 142 (e.g., mouse, keyboard, tablet, touch-sensitive interface, etc.) may also be coupled to the client device 102, as is generally known.

Figure 2:
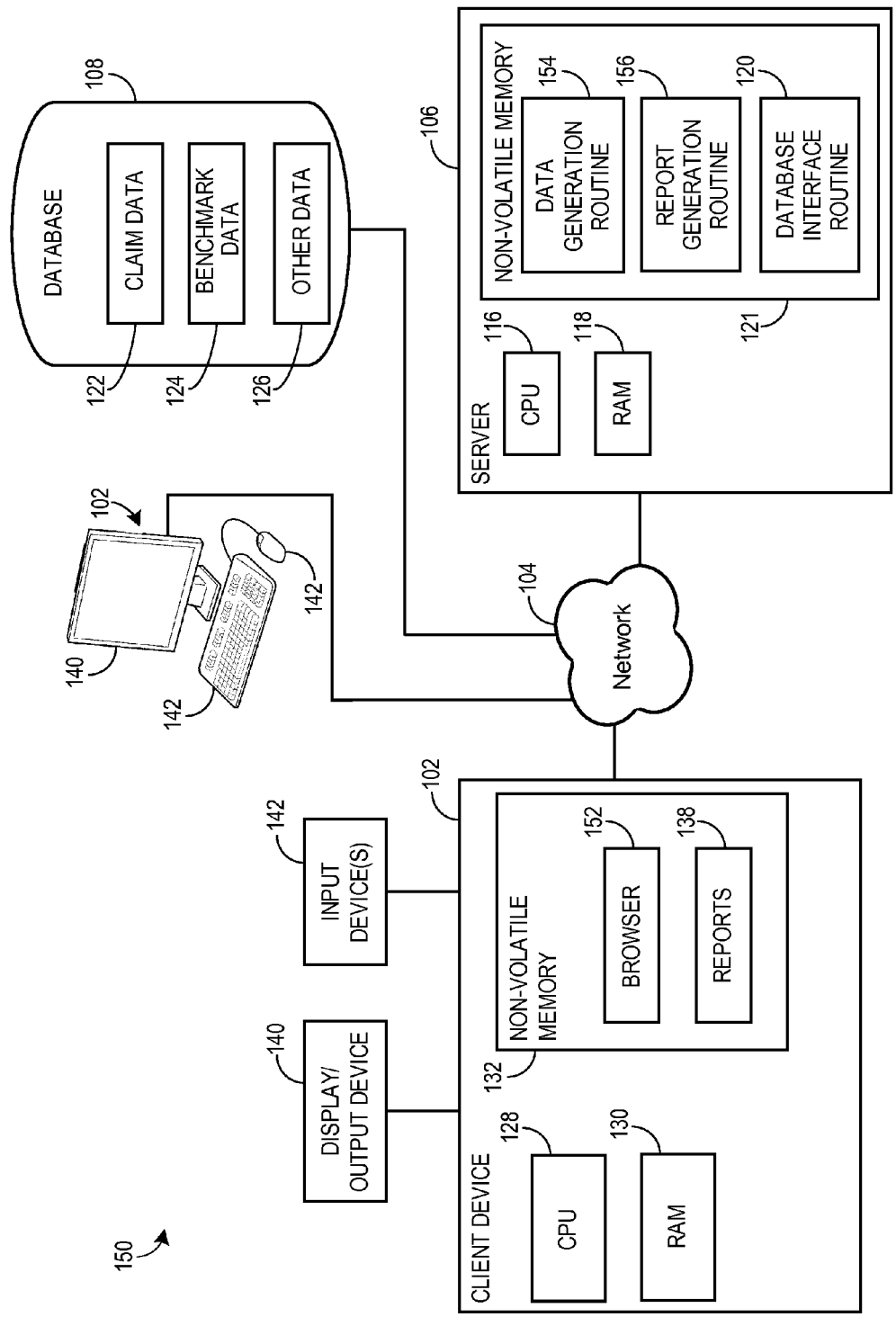
FIG. 2 is a block diagram of another embodiment of a system for generating a risk profile report.

Turning now to FIG. 2, a second embodiment 150 of the system 100 is depicted. Though similar in many respects to the embodiment 101 of the system 100 (depicted in FIG. 1), the embodiment 150 differs from the embodiment 101 in the routines stored in the non-volatile memories 121 and 132 of the server 106 and the client device 102, respectively. In the embodiment 150, the memory 132 stores a web browser routine 152 operable to communicate via the network 104 with the server 106 and, in particular, with one or more routines stored in the memory 121 thereof. Specifically, a report data generation routine 154 retrieves data from the database 108 and performs manipulation, tabulation, and calculation of data to generate information of the risk profile. The report data generation routine 154 may output the information of the risk profile to a report generation routine 156 in the server 106 that, in turn, may generate risk profile reports. The risk profile reports may be stored in the database 108, in the memory 121 of the server 106, or in as the reports 138 in the memory 132 of the client device 102. The routines 154 and 156 may receive data from, and pass data to, the browser routine 152 operating on the client device 102.

Regardless of whether the data generation routine is implemented in the client device 102 (e.g., as routine 134) or the server 106 (e.g., as routine 154), the data generation routine may be designed to process data retrieved from the database 108. Specifically, the data generation routine 134, 154 processes data to evaluate metrics in various risk categories. In an embodiment, there are 12 categories of metrics, each category related to losses, premiums and frictional costs, or claim administration. The categories of metrics include: premiums—the cost of insurance or the sum of money paid, usually at regular intervals, for an insurance policy; state pass-throughs—claim related expenses assessed by a jurisdiction (e.g., a state) and "passed through" to the insured by the qualified self insurer or the insurance company; collateral—funds, in an amount calculated by actuaries based upon the reserves of open claims and various development factors (e.g., credit sharing), from which future liabilities created by claims may be paid; medical strategy—management of medical costs associated with claims; prevention—management (i.e., reduction) of claim frequency; information management—use of information systems to monitor claim frequency and severity and claim reserve development; litigation management—management of litigation costs associated with claims; disability management—management of the processes related to returning an injured person to maximum medical improvement and returning them to work; actuarial processes—processes related to calculating liabilities associated with open claims to confirm that adequate capital (e.g., letters of credit or surety bonds) are reserved to cover future liabilities; claims process—the process from claim reporting through claim closure, required to effectively and efficiently manage a claim; program structure—the structure of the insurance program and its effects on premium versus liabilities, administration costs, and jurisdictional compliance; and coverage—the terms of an insurance policy specifying the items or hazards covered by the policy.

In each category, the specific metrics evaluated by the data generation routine 134, 154 may include metrics derived from claim data (e.g., the claim data 122 stored in the database 108) and/or metrics determined according to survey responses (e.g., the other data 126 stored in the database 108). The claim data 122 and the other data 126 (e.g., the survey responses) may be received from a client or insurer organization in response to a request from the entity providing the risk profile. For example, in an embodiment, a consultant has access to the client device 102. The consultant may request data from an insurance carrier or third-party administrator (TPA), and may request information from the client regarding non-claim aspects of the insurance program. In another embodiment, a user of the client device 102 has a more direct relationship with the insurance carrier or the TPA. For example, the user may be an employee of the insurer or TPA. In this embodiment, the user may have access to the necessary data and may need only to direct the data generation routine 134, 154 to a memory storage location (e.g., one or more files in the database 108) in which the data required by the routine 134, 154 is stored.

The data that will be used by the data generation routine 134, 154 may differ depending on the type of insurance and by the industry. For example, for certain businesses, it may be necessary to determine metrics related to workers' compensation claims only, while in other businesses it may be necessary to determine metrics related to workers' compensation and also to general and/or auto liability coverages.

The data request may include a request for multiple runs of data. Each run of data may include different sets of claims, different data for each claim, and/or different organization of data included in a different run. In an embodiment, the data are provided, in response to the request, in one or more worksheets of one or more spreadsheet documents. A request for data may include, for example, a request for a "loss run" related to workers' compensation claims. The request may specify that the loss run data should include data for some time period (e.g., three full calendar years, two fiscal years, the most recent 36 months, etc.), and may specify that the data should have current values and be sorted, for example, by loss year (i.e., the year that the loss occurred). The request may also specify that the loss run data should include all claims, whether open or closed. In an embodiment, the data request specifies specific fields to be included among the loss run data. By way of example and not limitation, the fields may (but need not necessarily in all embodiments) include: claim number, claimant name, date of loss, date claim reported to employer, date claim reported to carrier/TPA, claim status, date closed (if the claim is closed), date of hire (i.e., the employee hire date), date of birth or age of the employee, benefit state, jurisdiction, financials (broken out by medical, expense, indemnity and then by paid/outstanding and total incurred), location, occupation, department, cause of injury, source of injury, loss description, and body part affected.

A data request may also request a second run of data related to the workers' compensation claims. For example, the data request could request a payment summary report. Like the loss run, the data request may specify that the payment summary report should include data for a specific time period (e.g., two years of payment information), and may specify that the payment information should be valued as of "current" and sorted by loss year. The request may also specify that the data should include total summary of payments, and subtotals by major payment category (i.e., indemnity, medical, and expense). Further, the request may specify that the payment data include the number of claims (from the total claims) that include temporary total disability (TTD) payments and/or the number of claims with defense counsel and/or litigation expenses.

Further, a data request related to workers' compensation may also request a "converted claims" loss run including information on claims that have converted from medical claims to indemnity claims. Once again, the data request may specify that the converted claims report include claim data for a specific period (e.g., two years of claim information), may specify that the claim information should be valued as current and sorted by, for example, loss year, and may specify that the converted claims loss run should include all claims, both open and closed, for the requested time period. In an embodiment, the data request specifies specific fields to be included among the converted claims loss run data. By way of example and not limitation, the fields may (but need not necessarily in all embodiments) include: claim number, claimant name, date of loss, date the claim was reported, the claim status, the date the claim was closed (if it is closed), the employee hire date, the employee date of birth, the benefit state, jurisdiction, financials (broken out by medical, expense, and indemnity, and then by whether the claim is paid or outstanding and the total amount incurred), location, cause of injury, source of injury, loss description, and the affected body part.

Still further, a data request may include a request for program data including, but not limited to: a description of operations; a classification code (e.g., the North American Industry Classification System (NAICS) code) that fits the operations; an audited financial report; a latest actuarial report; a report of latest insurer loss forecasts for a retained layer by line of coverage; a collateral level breakdown by carrier, policy year, line of coverage, workers' compensation broken down by state, including any QSI states and assessments/surcharges by state; a report of the form of collateral (e.g., letters of credit, cash, etc.) and collateral estimated cost; a TPA contract(s) and/or a breakdown to TPA names reflecting the policy years and line(s) of coverage available from the TPA; a most recent TPA or carrier claim handling stewardship report; and/or casualty insurance program details including: policy periods; retentions and limits per line of coverage and policy period; exposure workers' compensation (e.g., including payroll by state and class code per policy year); exposure liability (e.g, including revenue and auto count/miles driven per policy year); captive use description and captive financials; primary casualty binder/financial program agreement; umbrella binders.

A data request may also include a request for information about preferred provider network penetration and/or a request for a most-recent actuarial report, including, for example, claim frequency rates by line of coverage for a specific time period (e.g., the most recent three years). Of course, the data request may, in some embodiments, include requests for more, less, or different information, depending on the particular risk categories to be evaluated and/or the particular metrics to be evaluated in each risk category.

The data received in response to the data request may be stored in the database 108. Specifically, claim data (loss runs, etc.) may be stored as the claim data 122, while answers to qualitative survey questions, actuarial reports, and other data may be stored as the other data 126.

Among other tasks, the data generation routine 134, 154 may perform tasks related to determining from the data provided one or more results, such as tabulating claims meeting certain criteria and calculating various averages, percentages, cost totals, etc., as described below. Each of the one or more results may be associated with a key performance indicator (KPI). The KPIs are metrics that are compared against one or more benchmark values to determine the role played by the metric, and the category with which the metric is associated, in terms of risk and loss.

Various examples of KPIs will be described in the following paragraphs, though their description is not intended to exclude other KPIs or to indicate that any one of the KPIs must be included in a particular embodiment, unless otherwise indicated. Additionally, the ordinal designation of the various metrics as "first," "second," "third," etc. is not intended to indicate an order in which the metrics are determined, as the metrics are described in no particular order and, in various embodiments, each may be included or excluded.

In an embodiment, the data generation routine 134, 154 determines a first metric associated with disability management. The first metric may be a percentage of workers' compensation claims that include TTD payments as a part of the total claim count. For example, if the loss run data include 3000 claims, and 612 of the claims include TTD payments, then 20.4% of the claims include TTD payments. After the report data generation routine 134, 154 determines the first metric, the routine 134, 154 may determine one or more benchmark values and may compare the result related to the first metric to the one or more benchmark values. In an embodiment, the routine 134, 154 retrieves benchmark data 124 stored in the database 108—from which benchmark values may be calculated—and calculates the benchmark values therefrom. In another embodiment, the routine 134, 154 retrieves benchmark values from the benchmark data 124 stored in the database 108. For example, the benchmark values may be stored in a table according to industry, time period, geographical region, etc.

In any event, the routine 134, 154 compares the first metric to the determined benchmark values and, according to the comparison, assigns a risk indication corresponding to the metric. The routine 134, 154 may determine that the benchmarks applicable for a given set of data should result in assignment of a negative indication if the first metric is greater than 70%, a positive indication if the first metric is less than 35%, and a moderate indication if the first metric is between 35% and 70%, for example. While various ranges and benchmark values are disclosed with respect to the metrics herein described, the ranges and benchmark values are exemplary only. The ranges and benchmark values may be any designated values stored as the benchmark data 124, including values calculated by one or more computer processors, such as data corresponding to an organization's peers within an industry, job classification, or jurisdiction.

In an embodiment, the data generation routine 134, 154 determines a second metric associated with disability management. The second metric may be an average number of TTD days per TTD claim. Determining the average number of TTD days per TTD claim may, in some instances, require multiple calculations. For example, if the loss run data include 612 claims that include TTD payments, the average TTD days per TTD claim may be calculated by dividing the total cost of TTD claims by the number of TTD claims (e.g., 612), and then dividing the average TTD cost per TTD claim by the average value of a TTD daily payment (e.g., $50). After the data generation routine 134, 154 determines the second metric, the routine 134, 154 may determine one or more benchmark values as described above, compare the result related to the second metric to the one or more benchmark values, and assign a risk indication corresponding to the metric (e.g., negative if the result of the second metric is more than 100 days, positive if less than 50 days, and moderate if between 50 and 100 days).

In an embodiment, the data generation routine 134, 154 determines a third metric associated with the claims process category. The third metric may be an average value of indemnity claims. To determine the average value of indemnity claims the data generation routine 134, 154 may determine the total number of indemnity claims and the total amount of indemnity paid, and divide the latter by the former. After the routine 134, 154 determines the third metric, the routine 134, 154 may determine one or more benchmark values for the third metric as described above, compare the result related to the third metric to the one or more benchmark values for the third metric, and assign a risk indication corresponding to the third metric (e.g., negative if the result of the second metric is more than $20,000, positive if less than $10,000, and moderate if between $10,000 and $20,000).

In an embodiment, the data generation routine 134, 154 determines a third metric associated with the claims process category. The third metric may be an average value of indemnity claims. To determine the average value of indemnity claims the data generation routine 134, 154 may determine the total number of indemnity claims and the total amount of indemnity paid, and divide the latter by the former. After the routine 134, 154 determines the third metric, the routine 134, 154 may determine one or more benchmark values for the third metric as described above, compare the result related to the third metric to the one or more benchmark values for the third metric, and assign a risk indication corresponding to the third metric (e.g., negative if the result of the third metric is more than $20,000, positive if less than $10,000, and moderate if between $10,000 and $20,000).

In an embodiment, the data generation routine 134, 154 determines a fourth metric associated with the claims process category. The fourth metric may be a conversion rate and, in particular, a medical-to-indemnity conversion rate. To determine the conversion rate, the routine 134, 154 may determine (e.g., by counting) the total number of claims and the number of claims that were opened as medical only and closed as indemnity claims, and divide the latter by the former. After the routine 134, 154 determines the fourth metric, the routine 134, 154 may determine one or more benchmark values for the fourth metric as described above, compare the result related to the fourth metric to the one or more benchmark values for the fourth metric, and assign a risk indication corresponding to the fourth metric (e.g., negative if the result of the fourth metric is more than 40%, positive if less than 10%, and moderate if between 10% and 40%).

In an embodiment, the data generation routine 134, 154 determines a fifth metric associated with the claims process category. The fifth metric may be a claim closure rate for workers' compensation and, specifically, may be a 12-month claim closure rate (i.e., the percentage of claims closed within 12 months). To determine the claim closure rate, the routine 134, 154 may determine the total number of claims and the number of claims that were closed within 12 months, and divide the latter by the former. After the routine 134, 154 determines the fifth metric, the routine 134, 154 may determine one or more benchmark values for the fifth metric as described above, compare the result related to the fifth metric to the one or more benchmark values for the fifth metric, and assign a risk indication corresponding to the fifth metric (e.g., negative if the result of the fifth metric is less than 50%, positive if more than 90%, and moderate if between 50% and 90%).

In an embodiment, the data generation routine 134, 154 determines a sixth metric associated with the claims process category. The sixth metric may be a claim report lag time. The claim report lag time indicates the length of time that elapsed between the date of the loss and the date that the loss was reported to the insurer/TPA. To determine the claim report lag time, the routine 134, 154 may determine the percentage of the total claims having a lag time of a certain period (e.g., 5 days) or less, or may determine the average lag time for all of the claims. After the routine 134, 154 determines the sixth metric, the routine 134, 154 may determine one or more benchmark values for the sixth metric as described above, compare the result related to the sixth metric to the one or more benchmark values for the sixth metric, and assign a risk indication corresponding to the sixth metric (e.g., negative if the result of the sixth metric is less than 50% of claims reported within the time period, positive if more than 90% were reported within the time period, and moderate if between 50% and 90% were reported within the time period; or negative if the result of the sixth metric is an average claim report lag time of 10 days, positive if 3 days, and moderate if between 3 and 10 days).

In an embodiment, the data generation routine 134, 154 determines a seventh metric associated with the claims process category. The seventh metric may be a characterization related to the effect on balance sheet of outstanding reserves. The characterization may be a response to a qualitative survey question included with the data request. For example, in an embodiment, the question is a multiple-choice question related to the impact of the outstanding reserves on the balance sheet. The routine 134, 154 may retrieve the response to the qualitative survey question from the database 108 (e.g., from the other data 126). The routine 134, 154 may determine one or more benchmark values for the seventh metric, each of which may correspond with one or more of the multiple-choice answers available to the person who answered the survey, compare the result related to the seventh metric to the one or more benchmark values for the seventh metric, and assign a risk indication corresponding to the seventh metric.

In an embodiment, the data generation routine 134, 154 determines an eighth metric associated with the medical strategy category. The eighth metric may be a ratio of medical costs paid to the total payments. To determine the ratio of medical costs paid to the total payments, the routine 134, 154 may determine the total amount of medical costs paid, determine the total amount of medical, indemnity, and expenses, and divide the former by the latter. After the routine 134, 154 determines the eighth metric, the routine 134, 154 may determine one or more benchmark values for the eighth metric as described above, compare the result related to the eighth metric to the one or more benchmark values for the eighth metric, and assign a risk indication corresponding to the eighth metric (e.g., negative if the result of the eighth metric is more than 75%, positive if less than 55%, and moderate if between 55% and 75%).

In an embodiment, the data generation routine 134, 154 determines a ninth metric associated with the medical strategy category. The ninth metric may be a ratio of pharmacy costs paid to the medical costs paid. To determine the ratio of pharmacy costs paid to the medical costs paid, the routine 134, 154 may determine the total amount of pharmacy costs paid, determine the total amount of medical costs paid, and divide the former by the latter. After the routine 134, 154 determines the ninth metric, the routine 134, 154 may determine one or more benchmark values for the ninth metric as described above, compare the result related to the ninth metric to the one or more benchmark values for the ninth metric, and assign a risk indication corresponding to the ninth metric (e.g., negative if the result of the ninth metric is more than 25%, positive if less than 10%, and moderate if between 10% and 25%).

In an embodiment, the data generation routine 134, 154 determines a tenth metric associated with the medical strategy category. The tenth metric may be a preferred provider organization (PPO) penetration rate. To determine the PPO penetration rate, the routine 134, 154 may retrieve a survey response from the data provided in response to the data request (e.g., from the other data 126). After the routine 134, 154 determines the tenth metric, the routine 134, 154 may determine one or more benchmark values for the tenth metric as described above, compare the result related to the tenth metric to the one or more benchmark values for the tenth metric, and assign a risk indication corresponding to the tenth metric (e.g., negative if the result of the tenth metric is less than 45%, positive if more than 75%, and moderate if between 45% and 75%).

In an embodiment, the data generation routine 134, 154 determines an eleventh metric associated with the litigation management category. The eleventh metric may be a percentage of the total claims that are litigated. To determine the percentage of total claims that are litigated, the routine 134, 154 may determine the number of claims that were litigated, may determine the total number of claims, and may divide the former by the latter. After the routine 134, 154 determines the eleventh metric, the routine 134, 154 may determine one or more benchmark values for the eleventh metric as described above, compare the result related to the eleventh metric to the one or more benchmark values for the eleventh metric, and assign a risk indication corresponding to the eleventh metric (e.g., negative if the result of the eleventh metric is more than 15%, positive if less than 5%, and moderate if between 5% and 15%).

In an embodiment, the data generation routine 134, 154 determines a twelfth metric associated with the litigation management category. The twelfth metric may be a ratio of expense costs (i.e., costs associated with the claim other than indemnity and medical payments, such as surveillance, attorney fees, expert testimony, witnesses and summonses, autopsy, copying, arbitration, appeal bond costs, appeal filing fees, etc.) to total costs paid. To determine the ratio of expense costs to total costs paid, the routine 134, 154 may determine the expense costs paid for all the claims, may determine the total costs paid for all the claims, and may divide the former by the latter. After the routine 134, 154 determines the twelfth metric, the routine 134, 154 may determine one or more benchmark values for the twelfth metric as described above, compare the result related to the twelfth metric to the one or more benchmark values for the twelfth metric, and assign a risk indication corresponding to the twelfth metric (e.g., negative if the result of the twelfth metric is more than 22%, positive if less than 7%, and moderate if between 7% and 22%).

In an embodiment, the data generation routine 134, 154 determines a thirteenth metric associated with the litigation management category. The thirteenth metric may be a ratio of legal expense costs to total expense costs paid. To determine the ratio of legal expense costs to total expense costs paid, the routine 134, 154 may determine the legal expense costs paid for all the claims, may determine the total expense costs paid for all the claims, and may divide the former by the latter. After the routine 134, 154 determines the thirteenth metric, the routine 134, 154 may determine one or more benchmark values for the thirteenth metric as described above, compare the result related to the thirteenth metric to the one or more benchmark values for the thirteenth metric, and assign a risk indication corresponding to the thirteenth metric (e.g., negative if the result of the thirteenth metric is more than 50%, positive if less than 25%, and moderate if between 25% and 50%).

In an embodiment, the data generation routine 134, 154 determines a fourteenth metric associated with the litigation management category. The fourteenth metric may be a response to a qualitative survey question related to litigation management efforts. To determine the response to the qualitative survey question, the routine 134, 154 may retrieve the survey response from the data provided in response to the data request (e.g., from the other data 126). The routine 134, 154 may determine one or more benchmark values for the fourteenth metric, each of which may correspond with one or more of the multiple-choice answers available to the person who answered the survey, compare the result related to the fourteenth metric to the one or more benchmark values for the fourteenth metric, and assign a risk indication corresponding to the fourteenth metric.

In an embodiment, the data generation routine 134, 154 determines a fifteenth metric associated with the litigation management category. The fifteenth metric may be a response to a qualitative survey question related to quality of litigation oversight. To determine the response to the qualitative survey question, the routine 134, 154 may retrieve the survey response from the data provided in response to the data request (e.g., from the other data 126). The routine 134, 154 may determine one or more benchmark values for the fifteenth metric, each of which may correspond with one or more of the multiple-choice answers available to the person who answered the survey, compare the result related to the fifteenth metric to the one or more benchmark values for the fifteenth metric, and assign a risk indication corresponding to the fifteenth metric.

In an embodiment, the data generation routine 134, 154 determines a sixteenth metric associated with the prevention category. The sixteenth metric may be an actuarially based claim frequency rate and, in particular, a claim frequency trend over a period of time. To determine the actuarially based claim frequency trend, the routine 134, 154 may retrieve the data from data provided as a response to the data request (e.g., from the other data 126). After the routine 134, 154 determines the sixteenth metric, the routine 134, 154 may determine one or more benchmark values for the sixteenth metric as described above, compare the result related to the sixteenth metric to the one or more benchmark values for the sixteenth metric, and assign a risk indication corresponding to the sixteenth metric (e.g., negative if the result of the sixteenth metric is a trend increasing by more than 15% over a given time period, positive if the trend is decreasing, and moderate if the trend shows an increase of less than 15% over the time period).

In an embodiment, the data generation routine 134, 154 determines a seventeenth metric associated with the prevention category. The seventeenth metric may be an Occupational Safety & Health Administration (OSHA) incidence rate. In some instances, the seventeenth metric may be determined as a variance of the OSHA incidence rate from an industry wide rate (e.g., the rate according to the Bureau of Labor Statistics). To determine the OSHA incidence rate, the routine 134, 154 may retrieve the data from data provided as a response to the data request (e.g., from the other data 126). After the routine 134, 154 determines the seventeenth metric, the routine 134, 154 may determine one or more benchmark values for the seventeenth metric as described above, compare the result related to the seventeenth metric to the one or more benchmark values for the seventeenth metric, and assign a risk indication corresponding to the seventeenth metric (e.g., negative if the result of the seventeenth metric is more than 10% above the industry rate, positive if the trend is more than 10% below the industry rate, and moderate if the metric is between 10% below and 10% above the industry rate).

In an embodiment, the data generation routine 134, 154 determines a eighteenth metric associated with the prevention category. The eighteenth metric may be a lost workday case rate (i.e., the rate of cases that include lost days of work). In some instances, the eighteenth metric may be determined as a variance of the lost workday case rate from an industry wide rate (e.g., the rate according to the Bureau of Labor Statistics). To determine the lost workday case rate, the routine 134, 154 may retrieve the data from data provided as a response to the data request (e.g., from the other data 126). After the routine 134, 154 determines the eighteenth metric, the routine 134, 154 may determine one or more benchmark values for the eighteenth metric as described above, compare the result related to the eighteenth metric to the one or more benchmark values for the eighteenth metric, and assign a risk indication corresponding to the eighteenth metric (e.g., negative if the result of the eighteenth metric is more than 10% above the industry rate, positive if the trend is more than 10% below the industry rate, and moderate if the metric is between 10% below and 10% above the industry rate).

In an embodiment, the data generation routine 134, 154 determines a nineteenth metric associated with the prevention category. The nineteenth metric may be a response to a qualitative survey question related to management support for internal initiatives to improve safety and prevention. For example, the question may request information about how a respondent would classify current initiatives focused on workers' compensation (or auto liability or product liability, etc.). To determine the response to the qualitative survey question, the routine 134, 154 may retrieve the survey response from the data provided in response to the data request (e.g., from the other data 126). The routine 134, 154 may determine one or more benchmark values for the nineteenth metric, each of which may correspond with one or more of the multiple-choice answers available to the person who answered the survey, compare the result related to the nineteenth metric to the one or more benchmark values for the nineteenth metric, and assign a risk indication corresponding to the nineteenth metric.

In an embodiment, the data generation routine 134, 154 determines a twentieth metric associated with the actuarial category. The twentieth metric may be a response to a qualitative survey question related to the method by which reserves are established. To determine the response to the qualitative survey question, the routine 134, 154 may retrieve the survey response from the data provided in response to the data request (e.g., from the other data 126). The routine 134, 154 may determine one or more benchmark values for the twentieth metric, each of which may correspond with one or more of the multiple-choice answers available to the person who answered the survey, compare the result related to the twentieth metric to the one or more benchmark values for the twentieth metric, and assign a risk indication corresponding to the twentieth metric.

In an embodiment, the data generation routine 134, 154 determines a twenty-first metric associated with the actuarial category. The twenty-first metric may be a response to a qualitative survey question related to the frequency of reserve reviews. To determine the response to the qualitative survey question, the routine 134, 154 may retrieve the survey response from the data provided in response to the data request (e.g., from the other data 126). The routine 134, 154 may determine one or more benchmark values for the twenty-first metric, each of which may correspond with one or more of the multiple-choice answers available to the person who answered the survey, compare the result related to the twenty-first metric to the one or more benchmark values for the twenty-first metric, and assign a risk indication corresponding to the twenty-first metric.

In an embodiment, the data generation routine 134, 154 determines a twenty-second metric associated with the actuarial category. The twenty-second metric may be a response to a qualitative survey question related to how premiums and loss costs are allocated to business units. To determine the response to the qualitative survey question, the routine 134, 154 may retrieve the survey response from the data provided in response to the data request (e.g., from the other data 126). The routine 134, 154 may determine one or more benchmark values for the twenty-second metric, each of which may correspond with one or more of the multiple-choice answers available to the person who answered the survey, compare the result related to the twenty-second metric to the one or more benchmark values for the twenty-second metric, and assign a risk indication corresponding to the twenty-second metric.

In an embodiment, the data generation routine 134, 154 determines a twenty-third metric associated with the data management category. The twenty-third metric may be a response to a qualitative survey question related to data analysis tools for analyzing claims, policies, and exposure. For example, the question may ask a respondent to select a response describing how data consolidation tools are being used. To determine the response to the qualitative survey question, the routine 134, 154 may retrieve the survey response from the data provided in response to the data request (e.g., from the other data 126). The routine 134, 154 may determine one or more benchmark values for the twenty-third metric, each of which may correspond with one or more of the multiple-choice answers available to the person who answered the survey, compare the result related to the twenty-third metric to the one or more benchmark values for the twenty-third metric, and assign a risk indication corresponding to the twenty-third metric.

In an embodiment, the data generation routine 134, 154 determines a twenty-fourth metric associated with the data management category. The twenty-fourth metric may be a response to a qualitative survey question related to claim report generation tools. For example, the question may ask a respondent to select the response that best describes the ease with which claim data collection is accomplished. To determine the response to the qualitative survey question, the routine 134, 154 may retrieve the survey response from the data provided in response to the data request (e.g., from the other data 126). The routine 134, 154 may determine one or more benchmark values for the twenty-fourth metric, each of which may correspond with one or more of the multiple-choice answers available to the person who answered the survey, compare the result related to the twenty-fourth metric to the one or more benchmark values for the twenty-fourth metric, and assign a risk indication corresponding to the twenty-fourth metric.

In an embodiment, the data generation routine 134, 154 determines a twenty-fifth metric associated with the data management category. The twenty-fifth metric may be a response to a qualitative survey question related to exposure report generation tools. As an example, the question may ask a respondent to describe the ease with which exposure data are collected. To determine the response to the qualitative survey question, the routine 134, 154 may retrieve the survey response from the data provided in response to the data request (e.g., from the other data 126). The routine 134, 154 may determine one or more benchmark values for the twenty-fifth metric, each of which may correspond with one or more of the multiple-choice answers available to the person who answered the survey, compare the result related to the twenty-fifth metric to the one or more benchmark values for the twenty-fifth metric, and assign a risk indication corresponding to the twenty-fifth metric.

In an embodiment, the data generation routine 134, 154 determines a twenty-sixth metric associated with the data management category. The twenty-sixth metric may be a response to a qualitative survey question related to the ease or difficulty of controlling data. To determine the response to the qualitative survey question, the routine 134, 154 may retrieve the survey response from the data provided in response to the data request (e.g., from the other data 126). The routine 134, 154 may determine one or more benchmark values for the twenty-sixth metric, each of which may correspond with one or more of the multiple-choice answers available to the person who answered the survey, compare the result related to the twenty-sixth metric to the one or more benchmark values for the twenty-sixth metric, and assign a risk indication corresponding to the twenty-sixth metric.

In an embodiment, the data generation routine 134, 154 determines a twenty-seventh metric. The twenty-seventh metric may be loss rate. In some embodiments, the loss rate may be determined as a function of a frequency rate and a severity rate. The frequency rate may be actuarially developed to measure total exposure. For example, the frequency rate may be determined by calculating the total number of claims for a unit exposure (e.g., the number of claims per $1,000 payroll). The severity rate may be actuarially developed to measure the average value of each claim (i.e., the total cost divided by the total number of claims). The loss rate, then, may be the total cost per unit exposure (e.g., the cost of losses per $1,000 payroll). The loss rate may be calculated using a historical loss run over a known period (e.g., 3 years, 5, years, 10 years, etc.). After the routine 134, 154 determines the twenty-seventh metric, the routine 134, 154 may determine one or more benchmark values for the twenty-seventh metric as described above, compare the result related to the twenty-seventh metric to the one or more benchmark values for the twenty-seventh metric, and assign a risk indication corresponding to the twenty-seventh metric. The benchmark value(s) for the twenty-seventh metric may be based on historical performance of the organization, on industry peer information stored in a database of public and/or proprietary information, or both. For example, the twenty-seventh metric may be calculated from data for a recent time period (e.g., the past three years) and compared to a benchmark value that is equal to the loss rate for the same organization from a previous time period (e.g., the three years before last). The risk indication may be assigned according to the trend for the organization (e.g., negative if the loss rate is trending higher by more than a certain amount, positive if the loss rate is trending lower by more than a certain amount, and moderate/neutral if the loss rate is steady or not changing by more than the certain amounts). Alternatively or additionally, the twenty-seventh metric may be calculated from data for a recent time period (e.g., the past three years) and compared to a benchmark value that is equal to the loss rate, over multiple peer organizations in an industry or organization type, for example, from the same period. The risk indication may be assigned according to the industry comparison (e.g., negative if the loss rate is higher than the peer companies by more than a certain amount, positive if the loss rate is lower than the peer companies by more than a certain amount, and moderate/neutral if the loss rate is similar to the peer companies).

In an embodiment, the data generation routine 134, 154 determines a twenty-eighth metric. The twenty-eighth metric may be a measure of state pass-throughs. As described above, state pass-throughs are frictional costs such as taxes, fees, and the like, that are paid to the state (or other governing jurisdiction). For example, Workers Compensation coverage is federally mandated, but premium rates vary by state, job classification, and other factors. In many states, insurers are able to write their own workers compensation plans, including determining whether to self-insure or insure through a deductible program (i.e., through an insurance company). As a result of the many variables, it is difficult to determine the optimal structure. In an embodiment, the twenty-eighth metric may be an average state pass-through value per unit exposure (e.g., per $1000 payroll). In some embodiments, the twenty-eighth metric may be further divided by geographic region, job classification, employee type, industry, etc. Thus, to determine the twenty-eighth metric, the report generation routine 134, 154 perform one or more of the following: determining the total amount of state pass-throughs paid to one or more jurisdictions, determining a total payroll value for each of the one or more jurisdictions, etc. After the routine 134, 154 determines the twenty-eighth metric, the routine 134, 154 may determine one or more benchmark values for the twenty-eighth metric as described above, compare the result related to the twenty-eighth metric to the one or more benchmark values for the twenty-eighth metric, and assign a risk indication corresponding to the twenty-eighth metric. For example, if the determined pass-through value per $1000 payroll for a particular jurisdiction is higher for the organization being evaluated than for the organization's peers, a negative risk indication may be assigned to the twenty-eighth metric.

In an embodiment, each of the risk indications may be a value associated with a cell in a spreadsheet, stored as a value in a record of the database 106, etc. For example, a negative risk indication may correspond to a "0" value, a moderate risk indication may correspond to a "1" value, a good risk indication may correspond to a "2" value, etc. In an embodiment, each risk indication is associated with color (e.g., red, yellow, green) so that a "dashboard" view may be presented to the user in a report. Of course, any system of risk indications may be used, including by way of example and not limitation, numerical indications (e.g., numbers 1-3 or 1-5) or scales, written descriptions (e.g., bad, moderate, good), arrows (e.g., down, side-to-side, up), icons (e.g., happy face, sad face, etc.) or any other easily interpreted indication.

Once the metrics have been evaluated, the benchmark values determined, the metrics compared to the benchmark values, and the risk indication assigned according to the comparisons, the system 100 may generate a report of the risk profile assessment. The report may be generated by the client device 102 running the report generation routine 136, as depicted in FIG. 1, in an embodiment. In an alternate embodiment, the report may be generated by the server 106 running the report generation routine 156. In either embodiment, the report data generation routine 134, 154, may call the report generation application 136, 156 (respectively) and may pass data from the data generation routine 134, 154 to the report generation routine 136, 156. The data passed may include the determined metrics, the benchmark values, and the assigned risk indications. Of course, in some embodiments, each of the report data generation routines 134, 154 and the report generation routines 136, 156 may be part of a larger application or routine, and the user may call each as desired by, for example, activating a user control (e.g., selecting a button or menu item) in the application.

FIG. 3 depicts one embodiment of a risk profile report 200 that may be generated by the system. The risk profile report 200 may, in some embodiments, take the form of a chart 202 with rows 204 corresponding to the KPIs and columns 206 corresponding to the relevant reported data. For example, the chart 202 depicted in FIG. 3 may include a row 204A related to the conversion rate KPI (i.e., medical-to-indemnity conversion rate). In a first column 206A, the chart 202 may include an indication of the metric (i.e. "Conversion Rate," "Medical-to-Indemnity Conversion Rate," or something similar). The first column 206A may also include, in embodiments, a brief description of the metric or, in embodiments, the description may be in a separate column or may be omitted entirely). A second column 206B includes the results associated with the metric. In the example above, the results associated with the conversion rate in row 204A, may include a simple value (e.g., 57%), a value and an indication of the time period (e.g., 2009: 57%), or a more descriptive statement (e.g., 57% of the indemnity claims in policy year 2009).

A third column 206C includes an representation 208 of the assigned risk indication. In the depicted example chart 202 in FIG. 3, the representation 208 takes the form of a "stoplight" assessment. That is, the representation 208 is a circle filled in with red, yellow, or green shading to indicate, respectively, a negative, moderate or positive risk indication. In FIG. 3, the respective shading is shown by cross-hatched, horizontal, and vertical lines. The use of a stoplight assessment allows a person viewing the report to get an immediate sense of which metrics could be significantly improved to reduce or optimize the risk profile. An explanation of the risk assessment may be provided in a column 206D. For example, the information in the column 206D may describe the criteria used to assess the metric and/or the reason for the indication (e.g., "Conversion rate is significantly higher than the industry best practice of 37%.")

The chart 202 may also include a column 206E making a recommendation for how to address any increased risk associated with a particular one of the metrics. For example, a recommendation for reducing the conversion rate may be provided for the example above or, for another metric the metric may be recommended to be watched because of a trend. By way of example and not limitation, the recommendations may include studying one or more factors (e.g., pricing, premiums, etc.) and/or reviewing practices and/or policies (e.g., claim review processes, litigation policies, etc.). The report generation routine 136, 156 may generate the recommendations according to one or more algorithms that receive as inputs one or more of the metrics and/or one or more of the assigned risk indications. The recommendations in the column 206E may also be based on combinations of the results. Because of this, in some embodiments, the recommendation may be provided outside of the chart 202, for example in a "recommendation" section of the report 200. The recommendation could also be included in one of the columns 206A-D, instead of in the column 206E.

Figure 4:
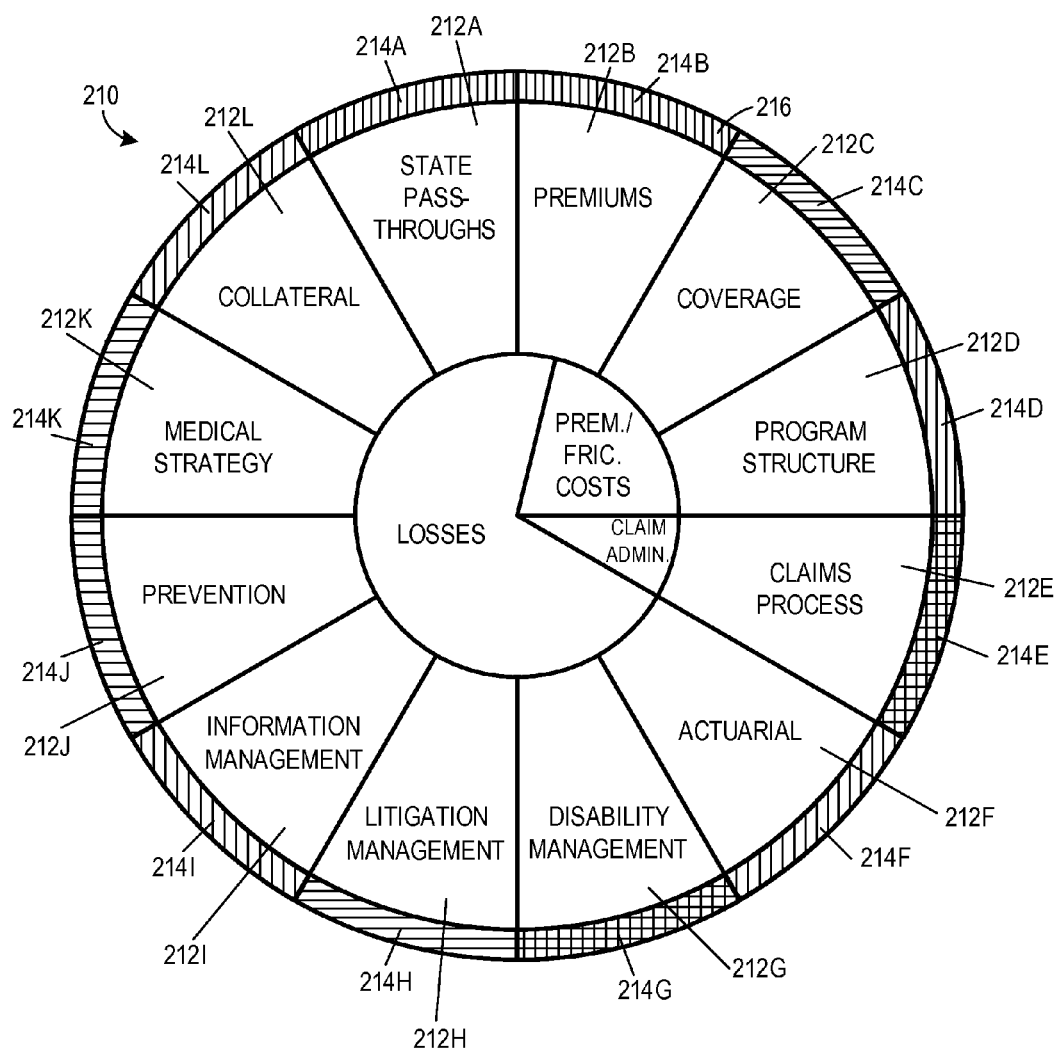
FIG. 4 illustrates a second aspect of the embodiment of the risk profile report of FIG. 3.

In some embodiments, the report 200 may also include a categorized risk assessment. FIG. 4 depicts one form that a categorized risk assessment could take. In the depicted embodiment, a circular chart 210 includes a sector 212 for each of the categories analyzed in the risk report. In the depicted chart 210, for example, sectors 212A-L represent the 12 categories included in the risk report. Each of the sectors 212A-L includes a corresponding indication 214A-L of the risk associated with the corresponding category. As depicted in FIG. 4, the indication 214A-L may be a colored area of an outer edge 216 of each of the sectors 214A-L, in an embodiment. In FIG. 4, for example, the edge 216 of each of the sectors 214A-L is shaded to reflect a negative, moderate, or positive risk assessment (represented as vertical, horizontal, or cross-hatched shading). In other embodiments, the entirety of the sector 212A-L may be colored to reflect the risk associated with the corresponding category. While the sectors 212A-L are depicted in FIG. 4 as equally sized, the sectors 212A-L are sized according to relative risk, ease of mitigating the risk, importance of the category as a loss driver, and/or potential savings, in an embodiment.

Additionally, while FIG. 4 depicts the chart 210 having 12 categories, the chart may have as many or as few categories as desired or as analyzed in the risk profile. For example, in an embodiment, the state pass-through category may be the only category considered in the report 200. In another embodiment, the actuarial category may be the only category considered in the report 200. Of course, the report 200 may include any single category described above or any combination of categories described above with or without additional categories. In an embodiment, the report 200 includes KPIs corresponding to both brokerage-related categories (e.g., premiums, coverage, and program structure) and loss-related categories (e.g., medical cost management, prevention, information management, litigation management, and disability management).

The risk assessment attributed to each of the categories may be assigned according to the risk indications assigned to the individual metrics associated with the category and, in particular, may be assigned according to the most negative assigned risk indication associated with the set of metrics, in an embodiment. For example, report lag time and conversion rate, each of which is associated with the claims process category, may have assigned negative and positive risk indications, respectively, in a particular report. Accordingly, the risk assessment attributed to the claims process category may be assigned as negative because the report lag time is assigned a negative risk indication. In another embodiment, the outer edge 216 of each sector 212A-L may be divided into a number of sub-sections corresponding to the number of KPIs associated with the respective category, and each sub-section may indicate the respective assigned risk indication of the KPI. For example, if only two KPIs (e.g., report lag time and conversion rate) are associated with a category (e.g., claims process), the edge 216 of the sector 212E may be divided into two sub-sections, one colored red (to indicate a negative assessment) and the other colored green (to indicate a positive assessment). As described above, the indications need not be red, yellow, and green and, in fact, need not be colors at all. Instead, the indications could be any appropriate indicator operable to provide a user with an easily interpreted view.

Figure 5:
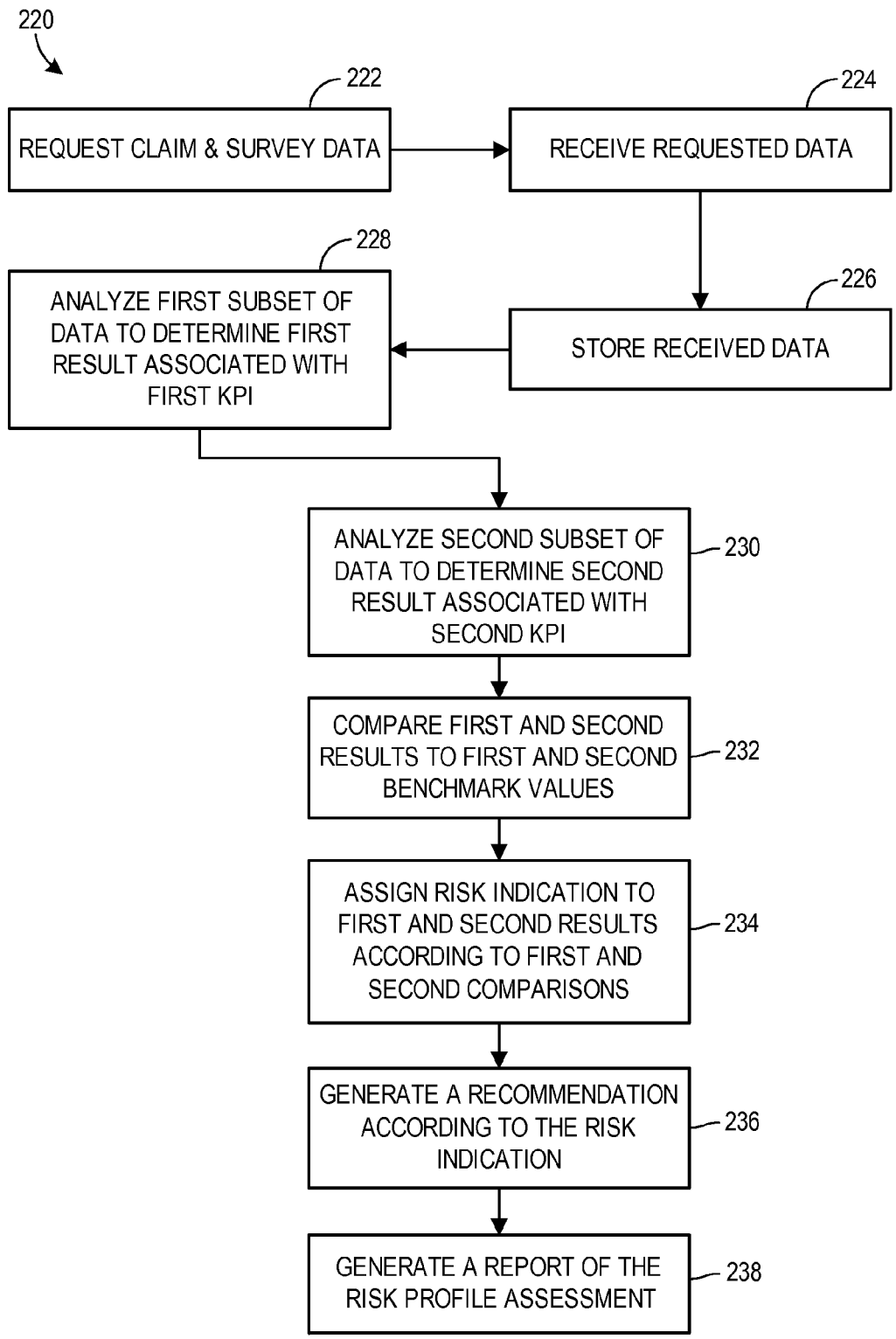
FIG. 5 is a flow chart depicting a method of generating a risk profile report in accordance with the present description.

Turning now to FIG. 5, a flow chart depicts a method 220 of assessing a risk profile. Generally, the method 220 starts with a request for claim data being sent to the entity requesting the risk assessment (block 222). The request may also include a request for data other than claim data and, specifically, may include a request for answers to a variety of questions characterizing and/or quantifying other aspects of the business, as generally described above with respect to various KPIs. Alternately, the request may be omitted, in some instances, where the data is already available to the entity performing the risk assessment.

The requested data and, optionally, other data (e.g., industry data, government data, etc.) may be received (block 224) and stored in the database 108 (block 226). Depending upon the exact implementation, receipt and/or storage of the data may be performed by the client device 102, the server 106, or a combination of the client device 102 and the server 106. In an embodiment, the data is sent to the server 106 and stored in the database 108 by the processor 116 using the database interface routine 120. In another embodiment, the client device 128 (specifically, the processor 128) receives the data and stores the data to the database 108 directly. In still another embodiment, the client device 128 receives the data and stores the data to the database 108 via the database interface routine 120 operating on the server 106.

In any event, having access to the stored data, the data generation routine 134 (or 154) analyzes a first subset of the data to determine a first result associated with a first KPI (block 228). For example, the data generation routine 134 (or 154) may analyze a payment summary report, qualitative survey data, one or more actuarial reports, one or more loss runs, etc., or a combination of these types of data to determine the first result. In embodiments, the data generation routine 134 (or 154) may analyze a second subset of the stored data to determine a second result associated with a second KPI (block 230). Depending on the particular KPI, determining the first result (and/or the second result) may require more than one determination and/or calculation. For instance, one KPI may require only a lookup of a survey response, while other KPIs may require tabulating claims to determine both a number of claims meeting a certain criterion and a total number of claims, and calculating a percentage based on the tabulated values. The first and second KPIs may be KPIs associated with a single categories (e.g., report lag time and conversion rate, both associated with the claims process category) or with different categories (e.g., conversion rate and percentage of claims with TTD payments, the latter of which is associated with the disability management category).

The data generation routine 134 (or 154) then compares the first and second results to corresponding first and second benchmark values (block 232). As will be appreciated based on the foregoing description, each of the first and second benchmark values, instead of being a single value, may be a set of values. That is, the data generation routine 134 (or 154) may compare the first result to a single value, as might be the case if there are only positive or negative risk indications available (e.g., compare the first result to the benchmark value to determine if the first result is above or below some value). Alternately, the data generation routine 134 (or 154) may compare the first result to multiple values, as might be the case if there are more than two risk indications available (e.g., compare the first result to a first value to determine if the first result is less than a first value, if it is then give a positive risk indication; if not, compare the first result to a second value to determine if the first result is greater than the second value, if it is then give a negative risk indication; if it is not, give a moderate risk indication). The data generation routine 134 (or 154) then assigns risk indications to each of the first and second results according to the first and second comparisons (block 234).

In some embodiments, a recommendation is generated according to the risk indication or risk indications (block 236) and/or, in some embodiments, according to the first and/or second results. The generation of the recommendation may be accomplished by the data generation routine 134 (or 154) or by the report generation routine 136 (or 156). The report generation routine 136 (or 156) generates a report of the risk profile assessment (block 238) according to the assigned risk indications and, in some embodiments, the generated recommendations. The report may be stored on the client device 102 or in the database 108.

Figure 6:
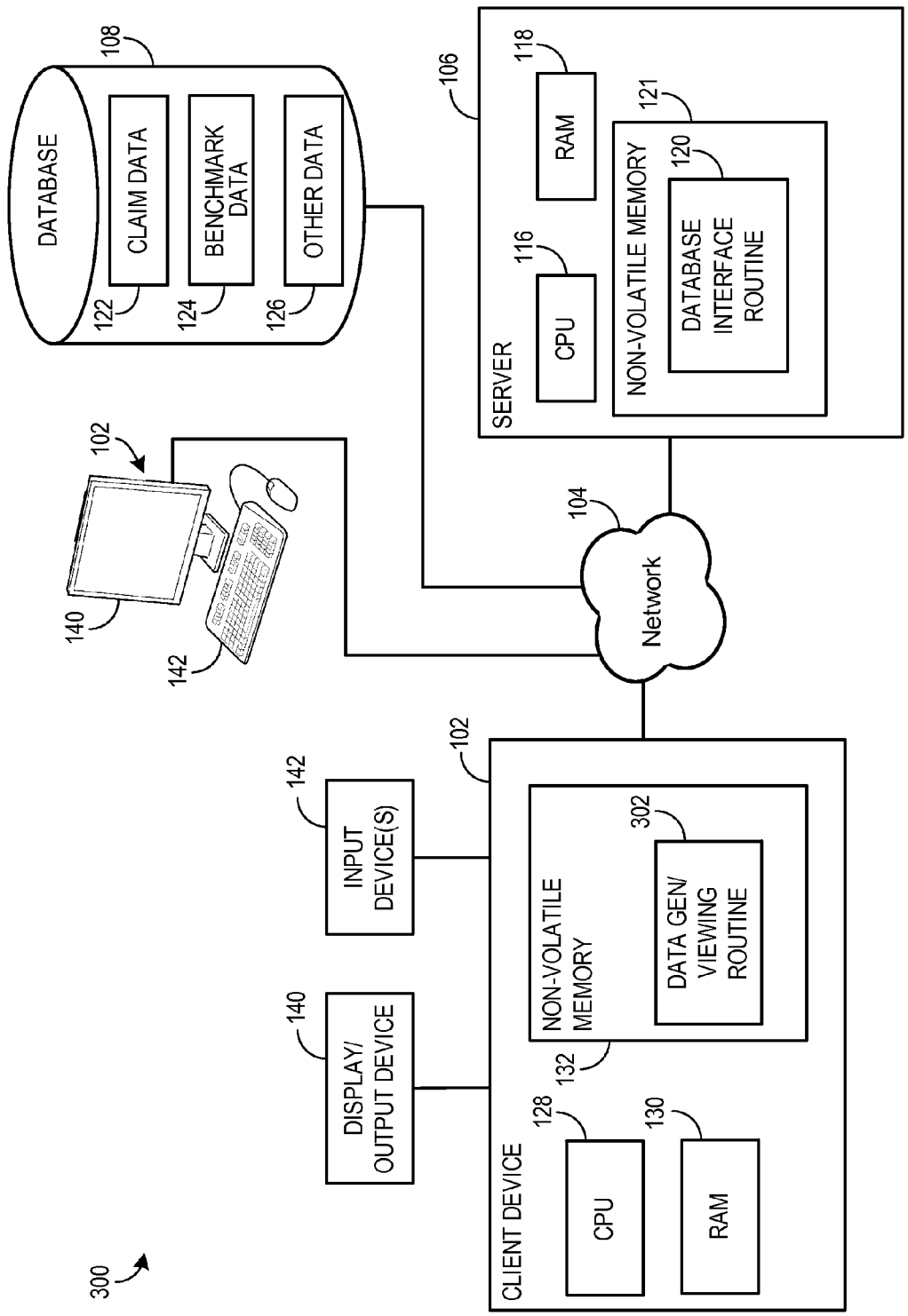
FIG. 6 is a block diagram of an embodiment of a system for displaying data associated with a risk profile.
Figure 7:
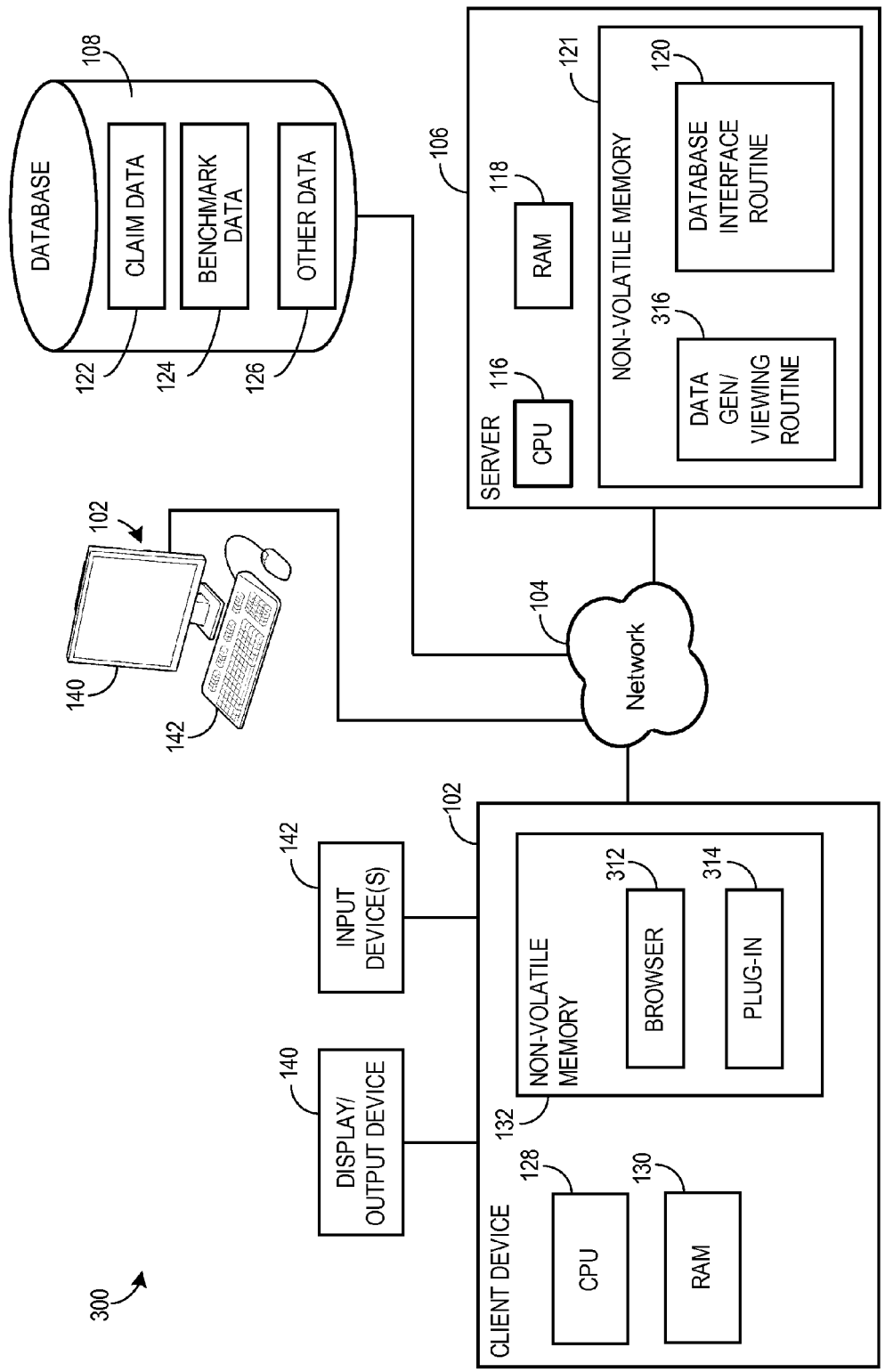
FIG. 7 is a block diagram of another embodiment of a system for displaying data associated with a risk profile.

In another embodiment, a routine may provide a user interface that both facilitates the analysis of one or more metrics and provides a means for accessing the data associated with the metric(s). FIGS. 6 and 7 depict embodiments 300 and 310 a system including the user interface routine. The embodiments 300 and 310 generally conform to the embodiments 101 and 150 depicted in FIGS. 1 and 2, but differ at least with respect to the routines stored in the non-volatile memories 132 (on the client device 102) and 121 (on the server 106). In particular, in the embodiment 300 depicted in FIG. 6, the non-volatile memory 132 includes a data generation and viewing routine 302. The routine 302, when executed by the processor 128, is operable to retrieve data from the database 108 (possibly via the database interface routine 120 on the server 106) and to determine one or more results associated with one or more KPIs. Additionally, in embodiments, the routine 302 is further operable to display the result over different time periods (e.g., over the past 1, 2, 3 years), to display the result at each of several times (e.g., October, November, December; or October 2009, October 2010, October 2011), to display a trend associated with the result, and/or to display the result relative to one or more benchmark values (e.g., as a marker placed along a divided continuum; as a bar graph with various reference values noted; etc.). The benchmark values may be stored locally on the client device 102. In an embodiment, the benchmark values may be updated occasionally via the network 104. Additionally, in some embodiments, the database 108 may be communicatively coupled to the client device 102, and/or the server 106 may be omitted.

The routine 302 further enables a user to see the data from which the result was determined, in an embodiment. For example, the routine 302 may receive a user input (e.g., a selection of a button, menu item, or feature of the graphical user interface) and, in response to the input, to display the associated data. Selection of a graph may open a new window (or replace the content of a current window) with a display of the data used to create the graph. In an embodiment, selection of a particular data point on a graph (e.g., a data point for the month of July) may cause the data for the month of July to be displayed to the user.

For some KPIs, the graphical information may depict subcategories of data, in an embodiment. As one example, an average indemnity cost may be displayed for each of several causes (e.g., slip/fall, caught in/between, struck/injured by, strain/overexertion, etc.). Additionally or alternatively, the average indemnity cost may be displayed for each of several months. As another example, an average indemnity cost may be displayed for each of several body parts injured (e.g., skin, bone/joint, soft tissue, etc.). As yet another example, an average indemnity cost may be displayed as a breakdown according to the organization (e.g., distributors, retail, manufacturing). Of course, the KPI for which results are displayed is not limited to average indemnity cost, but may include any KPI calculable from the available data including, without limitation, KPIs associated with the claims process, litigation management, disability management, and/or medical cost management categories.

In the embodiment 310 depicted in FIG. 7, the data generation and viewing functionality is implemented by the cooperation of a browser 312 operating on the client device 102 and a data generation and viewing routine 316 operating on the sever 106. Specifically, in an embodiment, the results associated with the KPI or KPIs may be generated in the data generation and viewing application 316 and may be formatted for transmission to the browser 312 which, in turn, may display the formatted results to the user. In an alternate embodiment, the a plug-in 314 may be installed with the browser, as generally known, and may implement the functionality of the data generation and viewing routine 316 or cooperate with the routine 316 to display the results.

Figure 8:
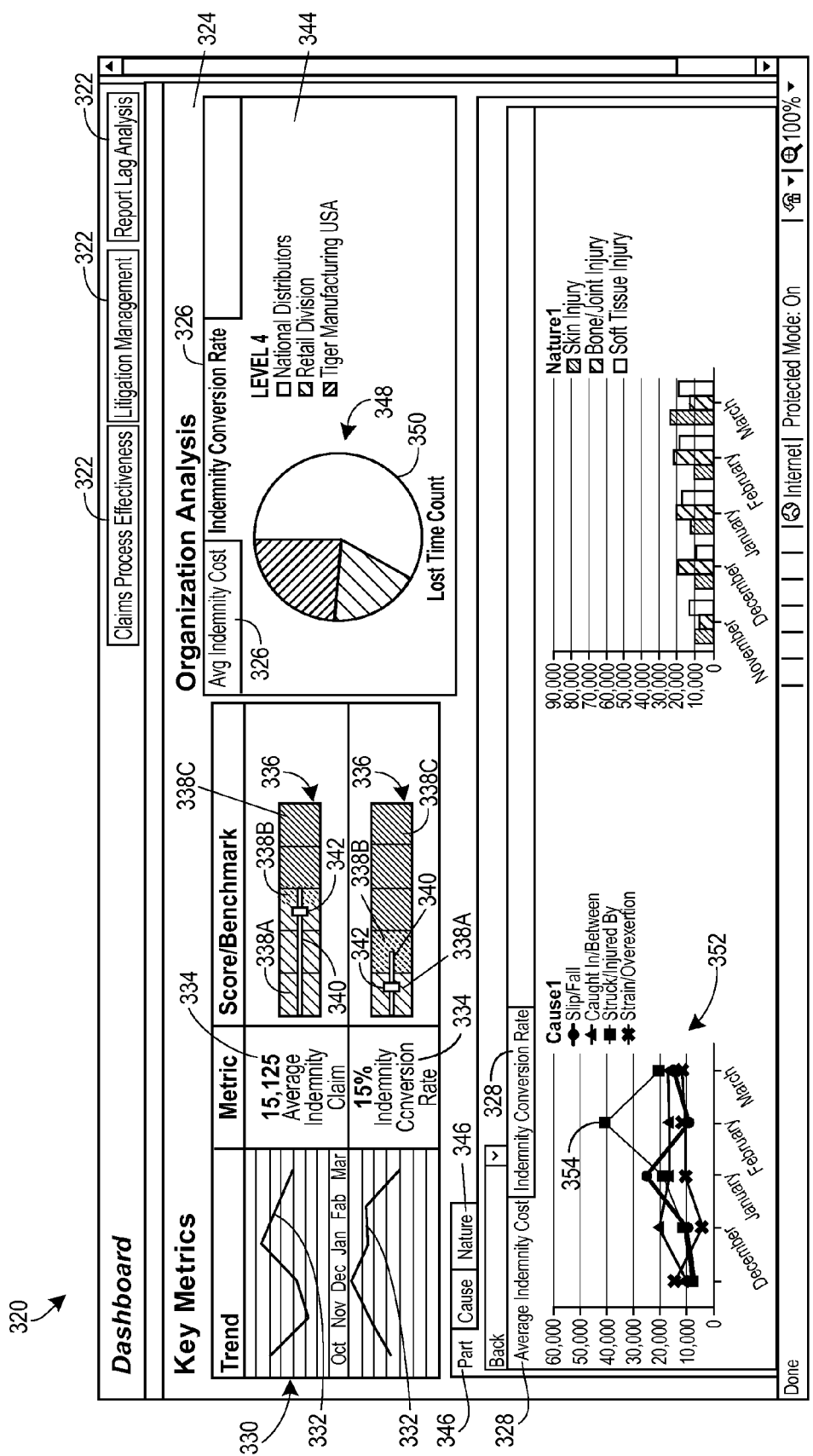
FIG. 8 illustrates aspects of a display generated by the system of FIG. 6 or FIG. 7.
Figure 9:
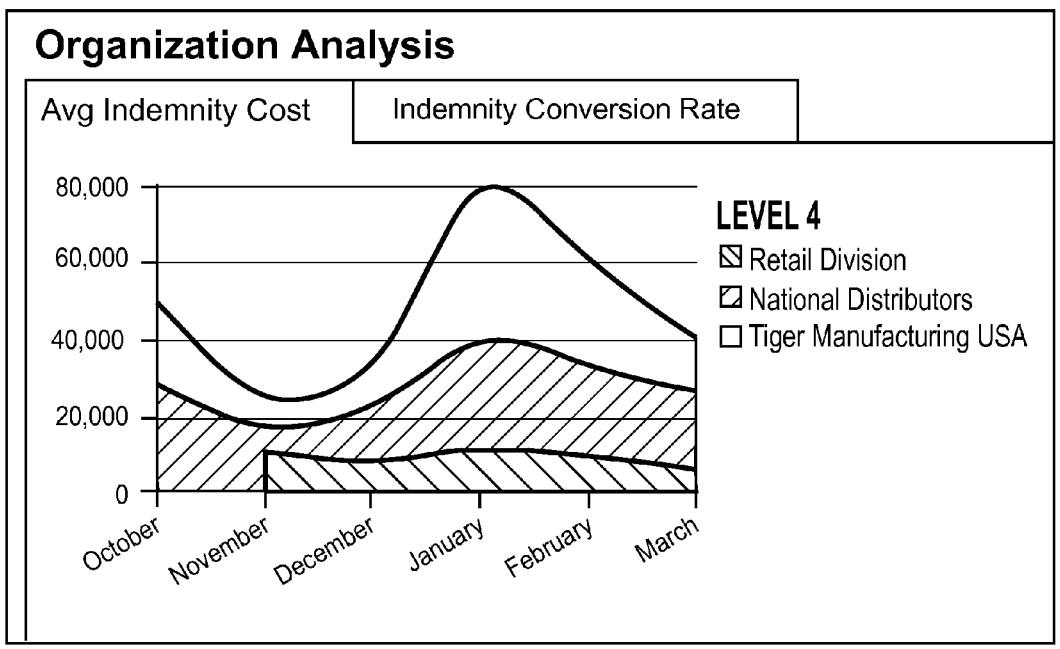
FIG. 9 illustrates additional aspects of a display generated by the system of FIG. 6 or FIG. 7.

FIGS. 8 and 9 illustrate various aspects of the GUI implemented, for example, by the embodiments 300 and 310. A display 320 includes controls 322 for selecting the categories of metrics (or, in some embodiments, the metrics) for display. A display area 324 displays the selected category of metrics and/or the selected metrics. In an embodiment, the display area 324 includes a sub-area corresponding to each of the metrics. In another embodiment, the display area 324 includes further controls (e.g., controls 326, 328) for selecting which metric to display in the display area 324.

A summary of the metrics may be displayed in one part 330 of the display area 324, in an embodiment. The summary may include, for each metric in the category selected to be displayed, a trend graph 332 for the data over some period of time, a value 334 of the result associated with the metric, and an indication 336 of how the result compares to the appropriate benchmark(s). In the exemplary display 320, the indication 336 is depicted as a continuum having three ranges 338A-C, a bar 340 indicating the range of the result over the depicted period of time, and a current result 342 corresponding to the most recent value of the result for the metric. In an alternate embodiment, the indication of how the result compares to the appropriate benchmark(s) may take the form of shading or other indicators on the trend graph 332.

The display area 324 may also include an organizational analysis of the KPIs in a second part 344. The organizational analysis may display the result for the KPI according to one or more parts of the organization as a whole showing, for example, the indemnity conversion rate among distributors, retailers, and manufacturers within the organization, as depicted in FIG. 8. In FIG. 8, the organizational analysis is presented as a pie graph 348. In an embodiment, selecting an area corresponding to one of the parts of the organization may cause the display to show the data corresponding to the area. For example, selecting segment 350 of the graph 348 corresponding to the distributors may cause the display to show the claim data corresponding to claims within the distributor part of the organization, which claims are part of the conversion rate calculation.

Further, the display area 324, by way of controls 346 may allow the user to select whether to view the data according to the body part injured, the cause of the injury, or the nature of the injury. Additional controls (not shown) may provide the user with the ability to specify different time periods for which data may be generated and/or displayed. Selecting a data point in one of the graphs may cause the display to show the set of data corresponding to the data point. For example, the display 320 illustrates a monthly average indemnity cost for each of four different causes in a graph 352. Selecting (e.g., with an input device) the data point 354 corresponding to the average indemnity cost for February of claims caused by being struck or injured by something may cause the data corresponding to the data point to be displayed.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

For example, the network 104 may include but is not limited to any combination of a LAN, a MAN, a WAN, a mobile, a wired or wireless network, a private network, or a virtual private network. Moreover, while only two client devices 102 are illustrated (only one in detail) to simplify and clarify the description, it is understood that any number of client device 102 are supported and can be in communication with the server 106.

Additionally, certain embodiments are described herein as including logic or a number of components, modules, routines, applications, or mechanisms. Applications or routines may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently or semi-permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments of a system and method for generating risk profile reports, and of a system and method for displaying data associated with a risk profile, for purposes of illustration only. One skilled in the art will readily recognize from the following discussion that alternative embodiments of the structures and methods illustrated herein may be employed without departing from the principles described herein.

Upon reading this disclosure, those of skill in the art will appreciate still additional alternative structural and functional designs for the disclosed systems and methods through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A memory device storing machine-readable instructions, the instructions executable by a processor to cause the processor to:

retrieve a first set of data from a database, the data including information about a plurality of insurance claims;

perform an analysis of the first set of data to determine a first result associated with a first key performance indicator (KPI);

obtain a first set of benchmark values corresponding to the first KPI;

compare the first result to the first set of benchmark values to determine the relationship of the first result to the set of benchmark values; and send to a display device a relationship between the first result and the first set of benchmark values, wherein the KPI is one of the group consisting of: a percentage of workers compensation claims that include temporary total disability (TTD) payments; an average number of days per TTD claim; an average value of indemnity claims; a medical-to-indemnity conversion rate; a claim closure rate for workers compensation claims; an average time between a date of loss and a date reported to a third party; a percentage of total claim payments attributable to medical costs; a percentage of medical costs attributable to pharmacy costs; a PPO penetration rate; a percentage of claims litigated; a percentage of total claim payments attributable to expenses; a percentage of total claim payments attributable to legal expenses; a trend relationship related to an actuarially based claim frequency rate; a variance related to an incidence rate of Occupational Safety & Health Administration (OSHA) claims; a variance related to a lost work date rate; and a loss rate calculated based on claim frequency and claim severity.

2. A memory device according to claim 1, wherein the instructions are further executable by the processor to cause the processor to:
perform an analysis of one or more second sets of data to determine one or more second results associated with one or more second key performance indicators;
obtain one or more second sets of benchmark values, each of the one or more second sets of benchmark values corresponding to a respective one of the one or more second key performance indicators;
compare each of the one or more second results to the respective one or more second sets of benchmark values; and
depict on the display device a relationship between each of the second results and each of the second sets of benchmark values.

3. A memory device according to claim 1, wherein the instructions are further executable by the processor to cause the processor to:
retrieve or calculate one or more previous values of the first result;
graphically depict the relationship between the determined first result and the one or more previous values of the first result.

4. A memory device according to claim 1, wherein the instructions are further executable by the processor to cause the processor to:
perform an analysis of one or more subsets of the first set of data to determine one or more second results associated with the first KPI; and
depict on the display device the relationship between first result and the one or more second results.

5. A memory device according to claim 1, wherein the first KPI is a medical-to-indemnity conversion rate determined according to the number of claims that start as medical-only claims and end as indemnity claims.

6. A memory device according to claim 1, wherein the first KPI is a loss rate and wherein determining a first result comprises:
determining a claim frequency rate; and
determining a claim severity rate.

7. A memory device according to claim 6, wherein:
determining a claim frequency rate comprises determining a claim count per unit of exposure; and
determining a claim severity rate comprises determining an average claim cost per unit of exposure.

8. A memory device according to claim 1, wherein the instructions are further executable by the processor to cause the processor to:
associate with the first KPI a risk indication according to the comparison of the first result to the first benchmark value; and
depict on the display device the first KPI and the risk indication associated with the first KPI.

9. A memory device according to claim 8, wherein the instructions are further executable by the processor to cause the processor to:
associate with each of the second one or more key performance indicators a respective risk indication according to the respective comparison of the one or more second results to the one or more second benchmark values; and
depict on the display device each of the second key performance indicators with the respective one or more associated risk indications.

10. A memory device according to claim 1, wherein the instructions are further executable by the processor to cause the processor to:
receive a selection input from a user; and
display a subset of the first set of data according to the selection input.

11. A memory device storing machine-readable instructions, the instructions executable by a processor to cause the processor to:
graphically depict on a display device a first category of risk analysis data related to a plurality of insurance claims;
graphically depict on the display device a relationship between a first analysis result and a first benchmark value corresponding to the first analysis result; and
graphically depict on the display device one or more user controls for selecting a second category of risk analysis data,
wherein the first analysis result is one of the group consisting of: a percentage of workers compensation claims that include temporary total disability (TTD) payments; an average number of days per TTD claim; an average value of indemnity claims; a medical-to-indemnity conversion rate; a claim closure rate for workers compensation claims; an average time between a date of loss and a date reported to a third party; a percentage of total claim payments attributable to medical costs; a percentage of medical costs attributable to pharmacy costs; a PPO penetration rate; a percentage of claims litigated; a percentage of total claim payments attributable to expenses; a percentage of total claim payments attributable to legal expenses; a trend relationship related to an actuarially based claim frequency rate; a variance related to an incidence rate of Occupational Safety & Health Administration (OSHA) claims; a variance related to a lost work date rate; and a loss rate.

12. A memory device according to claim 11, wherein depicting the relationship between the first analysis result and the first benchmark value comprises depicting for each of one or more key performance indicators (KPIs) associated with the first category at least:
a value calculated for the KPI; and
a comparison of the calculated value to a benchmark value.

13. A memory device according to claim 12, wherein the depicted information further includes for each KPI depicting one or more historical values corresponding to the calculated value.

14. A memory device according to claim 12, wherein a first of the one or more KPIs is a loss rate calculated based on claim frequency and claim severity.

15. A memory device according to claim 12, wherein a first of the one or more KPIs is a medical-to-indemnity conversion rate determined according to the number of claims that start as medical-only claims and end as indemnity claims.

16. A memory device according to claim 12, wherein the instructions are further executable by the processor to cause the processor to:
graphically depict for each KPI a relationship between each of a plurality of data subsets related to the KPI.

17. A memory device according to claim 16, wherein the plurality of data subsets comprises one or more of the group consisting of:
a data subset according to a time period;
a data subset according to a claim type;

a data subset according to an corporate organizational structure;

a data subset according to an injury type (injured part, injury cause, injury nature);

a data subset according to a claim value; and a data subset according to a relationship of claims to a benchmark value.

18. A memory device according to claim 16, wherein the instructions are further executable by the processor to cause the processor to:

receive a user input selecting one of the plurality of data subsets; and display in response to the received user input the data of the selected data subset.

19. A memory device according to claim 11, wherein the risk analysis data comprises insurance data of claims related to one of the group consisting of: workers' compensation, auto liability, and general liability.

20. A memory device according to claim 11, wherein the first category of risk analysis data comprises one of the group consisting of: claims process effectiveness, litigation management, and report lag analysis.

21. A memory device according to claim 11, wherein the instructions are further executable by the processor to the cause the processor to graphically depict a risk profile based on the risk analysis data.

* * * * *